United States Patent
Sato

(10) Patent No.: US 9,744,025 B2
(45) Date of Patent: Aug. 29, 2017

(54) BILE DUCT TUBE AND METHOD OF PLACING THEREOF

(71) Applicant: Takahiro Sato, Musashino (JP)

(72) Inventor: Takahiro Sato, Musashino (JP)

(73) Assignee: Takahiro Sato, Musashino-shi (JP)

( * ) Notice: Subject to any disclaimer, the term of this patent is extended or adjusted under 35 U.S.C. 154(b) by 522 days.

(21) Appl. No.: 14/032,874

(22) Filed: Sep. 20, 2013

(65) Prior Publication Data

US 2014/0024993 A1 Jan. 23, 2014

Related U.S. Application Data

(63) Continuation of application No. PCT/JP2011/001670, filed on Mar. 22, 2011.

(51) Int. Cl.

| A61M 5/00 | (2006.01) |
| A61F 2/04 | (2013.01) |
| A61B 17/12 | (2006.01) |
| A61F 5/00 | (2006.01) |
| A61B 17/00 | (2006.01) |
| A61B 90/00 | (2016.01) |

(52) U.S. Cl.

CPC .......... *A61F 2/04* (2013.01); *A61B 17/12036* (2013.01); *A61B 17/12136* (2013.01); *A61B 2017/00818* (2013.01); *A61B 2090/062* (2016.02); *A61F 5/0076* (2013.01); *A61F 2002/041* (2013.01)

(58) Field of Classification Search

CPC .................. A61F 2/04; A61F 2002/041; A61F 2025/1052; A61B 17/12036; A61B 17/12136; A61M 25/1011

See application file for complete search history.

(56) References Cited

U.S. PATENT DOCUMENTS 4,148,307 A * 4/1979 Utsugi ............... A61B 1/00156
600/115
5,188,595 A * 2/1993 Jacobi ................ A61M 25/1011
604/176

(Continued)

FOREIGN PATENT DOCUMENTS

| JP | 59-71647 U | 5/1984 |
| JP | 2002-143311 A | 5/2002 |

OTHER PUBLICATIONS

WebMD: Esophagitis—Topic Overview (https://web.archive.org/web/20090210163616/http://webmd.com/digestive-disorders/tc/esophagitis-topic-overview, Feb. 10, 2009, accessed Jun. 15, 2016, hereinafter WebMD).*

(Continued)

*Primary Examiner* — Tatyana Zalukaeva
*Assistant Examiner* — Ariana Zimbouski
(74) *Attorney, Agent, or Firm* — Westerman, Hattori, Daniels & Adrian, LLP

(57) ABSTRACT

A bile duct tube has a first portion which has a first end portion of the bile duct tube and is formed to have a diameter that allows insertion into a bile duct, a second portion which has a second end portion of the bile duct tube and is formed to have a diameter that allows insertion into an intestinal tract, and a first expansion member placed at the first portion. The first expansion member expands in a radial direction of the bile duct tube when a gas or liquid is injected into a void inside the first expansion member.

18 Claims, 7 Drawing Sheets

(56) References Cited

U.S. PATENT DOCUMENTS

| | | | | |
|---|---|---|---|---|
| 5,312,343 | A | * | 5/1994 | Krog .................. A61M 25/1011 604/101.03 |
| 2004/0092892 | A1 | * | 5/2004 | Kagan ....................... A61F 2/04 604/264 |
| 2005/0085787 | A1 | * | 4/2005 | Laufer ................ A61B 17/1114 604/500 |
| 2008/0255550 | A1 | * | 10/2008 | Bell ....................... A61B 18/04 606/21 |

OTHER PUBLICATIONS

Ryan Am, et al., "Barrett Esophagus: Prevalence of Central Adiposity, Metabolic Syndrome, and a Proinflammatory State", Annals of Surgery (2008),vol. 247, pp. 909-915; cited in Specification.

Tack J. et al., "Gastroesophageal Reflex Disease Poorly Responsive to Single-Dose Proton Pump Inhibitors in Patients without Barretts's Esophagus: Acid Reflux, Bile Reflux, or Both?", American Journal of Gastroenterology. (2004), 99, pp. 981-988; cited in Specification.

Pace F. et al., "Biliary reflux and non-acid reflux are two distinct phenomena: A comparison between 24-hour multichannel intraesophageal impedance and bilirubin monitoring", Scandinavian Journal of Gastroenterology, (2007), 42, pp. 1031-1039; cited in Specification.

Sato T et al., "Long-Term Postoperative Functional Evaluation of Pylorus Preservation in Imanaga Pancreatoduodenectomy", Digestive Diseases and Science (2000), 45, pp. 1907-1912; cited in Specification.

Sato T et al., "A New Examination for Both Biliary and Gastrointestinal Function after Pancreatobiliary Surgery-Single-isotope Two-day Method", Hepato-Gastroenterology (2000), 47, pp. 140-142; cited in Specification.

Miwa K et al., "Reflux of Duodenal or Gastro-Duodenal contents induces Esophageal Carcinoma in rats", Int. J. Cancer (1996), 67, pp. 269-274; cited in Specification.

Sato T et al., "The Sequential Model of Barrett's Esophagus and Adenocarcinoma Induced by Duodeno-esophageal Reflux without Exogenous Carcinogens", Anticancer Research (2002), 22, pp. 39-44; cited in specification.

Nishijima T et al., "Impact of the Biliary Diversion Procedure on Carcinogenesis in Barrett's Esophagus Surgically Induced by Duodenoesophageal reflux in Rats", Annals of Surgery (2004), 240, pp. 57-67; cited in Specification.

Ren CJ etal., "Early Results of Laparoscopic Biliopancreatic Diversion with Duodenal Switch : A Case Series of 40 Consecutive Patients", Obesity Surgery (2000), 10, pp. 514-523; cited in Specification.

Franzen T et al., "Long-term outcome is worse after laparoscopic than after conventional Nissen fundoplication", Scandinavian Journal of Gastroenterology (2005), 40, pp. 1261-12868; cited in Specification.

International Search Report for PCT/JP2011/001670, Mailing Date of Jun. 7, 2011.

Tessier DJ et al., "Surgical Management of Morbid Obesity", Curr Probl Surg, Feb. 2008, pp. 68-137, cited in specification.

Bais J. E. et al., "Laparoscopic or conventional Nissen fundoplication for gastroesophageal reflux disease: randomised clinical trial", The Lancet, vol. 355, Jan. 15, 2000, pp. 170-174, cited in specification.

* cited by examiner

BILE DUCT TUBE AND METHOD OF PLACING THEREOF

This application is a continuation of International Patent Application No. PCT/JP2011/001670 filed on Mar. 22, 2011, the entire content is incorporated herein by reference.

BACKGROUND OF THE INVENTION

Field of the Invention

The present invention relates to a bile duct tube and, more particularly, to a biliary diversion tube.

Description of the Related Art

It is said that in recent years, the eating habits of Japanese have become westernized. As a result, some of the diseases common to Japanese have been reduced, whereas diseases and reflux esophagitis accompanying overnutrition such as metabolic syndrome (visceral fat syndrome and the like) and the like have been increasing.

Metabolic syndrome is one of the diseases that modern people are facing. According to the summary of the national health and nutrition survey results reported in 2006 by Office for Lifestyle Related Diseases Control, General Affairs Division, Health Service Bureau, Ministry of Health, Labour and Welfare, there were estimated about 9,200,000 metabolic syndrome patients and 9,800,000 potential patients in Japan in 2005. The excessive intake and absorption of fat can be considered as one of the causes of metabolic syndrome. Men and women over 20 years of age tended to gradually decrease in energy intake, but gradually increased in fat energy ratio from 2002 to 2006.

The absorption of fat is deeply related to the dynamics of bile. That is, bile breaks down fat to allow absorption of fat. The present inventors have demonstrated by using radioisotope that in a long-term postoperative course, the miscible state of bile and ingested food influences nutrient absorption, in particular, the recovery of body weight (NPLs 4 and 5).

Both reflux esophagitis and Barrett's esophagus are disorders that have recently been on increase and have already been on rapid increase in Europe and the United States. They tend to increase in Japan following Europe and the United States. It has been affirmatively reported that these disorders are deeply related to each other (NPL 1). The important factors of reflux esophagitis include not only acid reflux but also esophageal reflux of bile (NPLs 2 and 3). The present inventors have demonstrated by preparing a duodenal juice regurgitation model after total gastrectomy in animal experiments that there is a pathological process of reflux esophagitis→Barrett's esophagus→esophageal adenocarcinoma without using any carcinogenic agent and without any involvement of gastric acid (NPLs 6 and 7).

As a medical treatment for morbid obesity, Bariatric surgery for suppressing nutrient absorption has been practiced. This medical treatment shows an increasing tendency, in particular, in the United States (NPL 9). Operative procedures for the purpose of obesity treatment include RYGB (Roux-en Y gastric bypass), adjustable gastric banding, vertical banded gastroplasty, sleeve gastrectomy, and biliopancreatic diversion. In consideration of minimal invasiveness, these procedures have come to be performed by using laparoscopes (NPL 10).

It has been proved that preemptive surgery for bile reflux is effective in suppressing the occurrence of Barrett's esophagus and esophageal adenocarcinoma (NPL 8). As surgical treatments for reflux esophagitis, Nissen's fundoplication and Toupet surgery have been performed for a long time. They are effective in regurgitation prevention. Like obesity treatment surgery, preemptive surgery for bile reflux has also been performed by using a laparoscope (NPLs 11 and 12).

CITATION LIST

Non Patent Literature

NPL 1: Ryan A M, Healy L A, Power D G, Byrne M, Murphy S, Byrne P J, Kelleher D, Reynolds J V. Barrett Esophagus: Prevalence of Central Adiposity, Metabolic Syndrome, and a Proinflammatory State. Ann Surg 2008; 247: 909-915.

NPL 2: Tack J, Koek G, Demedts I, Sifrim D, Janssens J. Gastroesophageal reflux disease poorly resdponsive to single-dose proton pump inhibitors in patients without Barrett's esophagus: acid reflux, bile reflux, or both? Am J Gastroenterol. 2004; 99: 981-988.

NPL 3: Pace F, Sangaletti O, Pallotta S, Molteni Porro G B. Biliary reflux and non-acid reflux are two distinct phenomenan: a comparison between 24-hour multichannel intraesophageal ompedance and bilirubin monitoring. Scand J Gastroenterol. 2007: 42: 1031-1039.

NPL 4: Sato T, Konishi K, Yabushita K, Kimura H, Maeda, K, Tsuji, M, Kinuya K, Nakajima K. Long-term postoperative functional evaluation of pylorus-preservation in Imanaga pancreatodudenectomy. Digestive Diseases and Sciences 2000, 45: 1907-191.

NPL 5: Sato T, Konishi K, Yabushita K, Kimura H, Maeda, K, Tsuji, M, Kinuya K, Nakajima K. A new examination for both biliary and gastrointestinal function after pancreatobiliary surgery—Single-isotope two-day method—. Hepato-gastroenterology 2000, 47: 140-142.

NPL 6: Miwa K, Sahara H, Segawa M, Kinami S, Sato T, Miyasaki I. Reflux of duodenal or gastro-duodenal contentents induces esophageal carcinoma in rats. Int. J Cancer 1996, 67: 269-274.

NPL 7: Sato T, Miwa K, Sahara H, Segawa M, Hattori T. The sequential model of Barrett's esophagus and adenocarcinoma induced by duodeno-esophageal reflux without exogenous carcinogens. Anticancer Research 2002, 22: 39-44.

NPL 8: Nishijima K, Miwa K, Miyashita T, Kinami S, Ninomiya I, Fushida S, Fujimura T, Hattori T. Impact of the biliary diversion procedure on carcinogenesis in Barrett's esophagus surgically induced by duodenoesophageal reflux in rats. Ann Surg 2004, 240: 57-67.

NPL 9: Tessier D J, et al: Surgical management of morbid obesity. Curr Probl Surg 45: 63-137, 2008.

NPL 10: Ren C J, Patterson E, Gagner M. Early results of laparoscopic biliopancreatic diversion with duodenal switch: a case series of 40 consecutive patients. Obes Surg. 2000, 10: 514-523.

NPL 11: Bais J E, Bartelsman J F, Bonjer H J, Cuesta M A, Go P M, Klinkenberg-Knol E C, van Lanschot J J, Nadorp J H, Smout A J, van der Graaf Y, Gooszen H G. Laparoscopic or conventional Nissen fundoplication for gastrooesophageal reflux disease: randomised clinical trial. The Netherlands Antireflux Surgery Study Group. Lancet. 2000, 355: 170-174.

NPL 12: Franzen T, Anderberg B, Wiren M, Johansson K E. Long-term outcome is worse after laparoscopic than after conventional Nissen fundoplication. Scand J Gastroenterol. 2005, 40: 1261-1268.

SUMMARY OF THE INVENTION

According to an embodiment, a bile duct tube comprises:

a first portion which has a first end portion of the bile duct tube and is formed to have a diameter that allows insertion into a bile duct;

a second portion which has a second end portion of the bile duct tube and is formed to have a diameter that allows insertion into an intestinal tract; and a first expansion member placed at the first portion, wherein the first expansion member expands in a radial direction of the bile duct tube when a gas or liquid is injected into a void inside the first expansion member.

According to another embodiment, a method of placing a bile duct tube in a body comprises:

inserting a first end portion of the bile duct tube into a bile duct from an intestine duodenum; and injecting a gas or liquid into a void inside a first expansion member placed at a first portion of the bile duct tube so that the first expansion member expands in a radial direction of the bile duct tube, wherein the first portion has the first end portion.

According to still another embodiment, a method of placing a bile duct tube in a body comprises:

a step of inserting a first end portion of the bile duct tube into a bile duct from an intestine duodenum; and a step of placing a second end portion of the bile duct tube in a digestive organ nearer to an anus than an intersection point between the intestine duodenum and the bile duct.

Other features and advantages of the present invention will be apparent from the following description taken in conjunction with the accompanying drawings. Note that the same reference numerals denote the same or like components throughout the accompanying drawings.

BRIEF DESCRIPTION OF THE DRAWINGS

The accompanying drawings, which are incorporated in and constitute a part of the specification, illustrate exemplary embodiments of the invention and, together with the description, serve to explain the principles of the present invention.

DESCRIPTION OF THE EMBODIMENTS

The embodiments of the present invention will be described below with reference to the accompanying drawings. However, the scope of the present invention is not limited to the following embodiments.

With advances in laparoscopic surgery, obesity treatment surgery and reflux esophagitis surgery have become less invasive. However, laparoscopic surgery accompanies surgical invasiveness, and hence it is not possible to ignore the occurrence of a complication. Therefore, a less invasive treatment method is expected to be developed.

According to at least one embodiment, it is possible to implement a less invasive treatment method for obesity or reflux esophagitis.

First Embodiment

A tube 100 according to an embodiment of the present invention will be described in detail below. The tube 100 is a bile duct tube. The tube 100 is inserted into the bile duct to carry bile into a digestive organ, as will be described later.

<Structure of Tube According to Embodiment>

Figure 3:
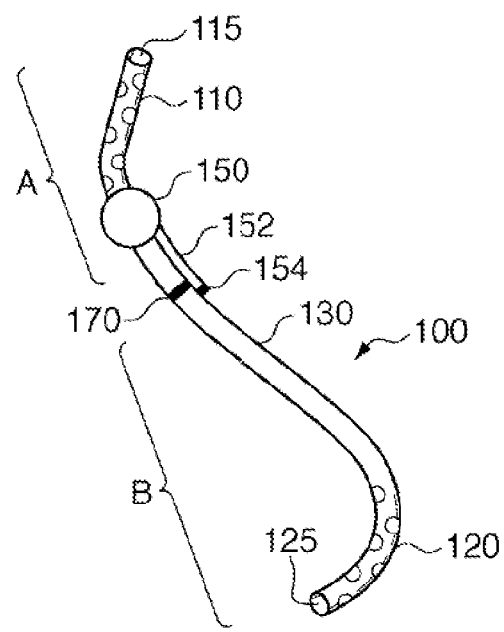
FIG. 3 is a view showing the outer appearance of the tube 100 according to the embodiment of the present invention.
Figure 4A:
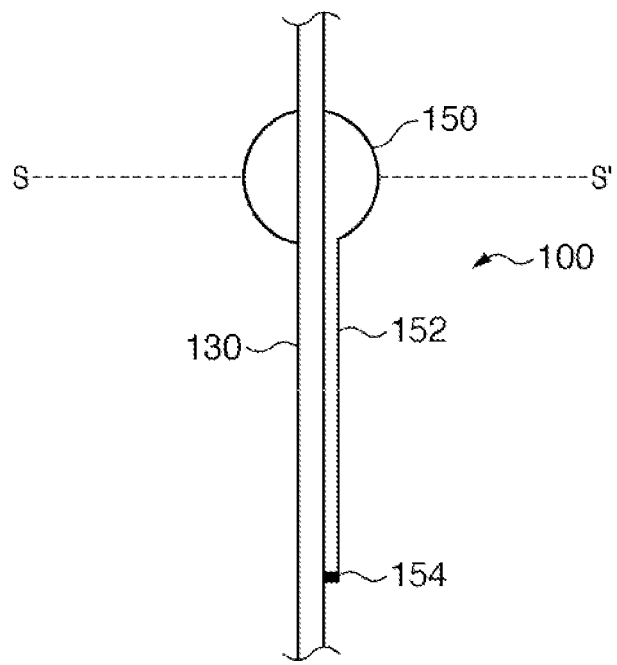
FIG. 4A is a sectional view of the tube 100 according to the embodiment of the present invention.

FIG. 3 shows the outer appearance of the tube 100 according to this embodiment. FIG. 4A is a sectional view of the tube 100 according to the embodiment when viewed from a direction parallel to the tube 100. As shown in FIG. 3, the tube 100 according to the embodiment includes a tube main body 130 and at least one expansion member (balloon 150). The following will exemplify the dimensions of each portion of the tube 100 according to the embodiment. However, the tube 100 according to the embodiment is not limited to the following. For example, the tube 100 can be suitably used for male adults. However, when using such tubes for children, it is possible to use tubes with smaller dimensions.

The inner diameter of the tube 130 according to this embodiment may be 0.5 mm or more, and may be 1 mm or more. In addition, the inner diameter may be 4 mm or less, may be 2 mm or less, and may be 1.5 mm or less. The larger the inner diameter, the more smoothly bile can flow. The smaller the inner diameter, the more the strength of the tube 130 can be increased.

The outer diameter of the tube 130 according to this embodiment may be 2.5 mm or more, and may be 3 mm or more. In addition, the outer diameter may be 5 mm or less, and may be 4 mm or less. The larger the outer diameter, the more the strength of the tube 130 can be increased. The smaller the outer diameter, the more easily the tube can be inserted into the bile duct.

The thickness of the tube 130 according to this embodiment may be 0.1 mm or more, and may be 0.2 mm or more. In addition, the thickness may be 1.5 mm or less, may be 1.0 mm or less, and may be 0.5 mm or less. The larger the thickness of the tube 130, the more the strength of the tube 130 can be increased. The smaller the thickness, the higher the flexibility of the tube 130. This facilitates placing the tube 130.

The length of the tube 130 according to this embodiment may be 1,400 mm or more, and may be 1,500 mm or more. In addition, the length may be 1,800 mm or less, and may be 1,700 mm or less. Letting the tube 130 have a sufficiently large length can make bile flow to the intestinum ileum. In contrast, not letting the tube 130 be too long can reduce stimulus to the intestine.

The material to be used for the tube 130 is not specifically limited but can have a strength high enough not to be damaged when the tube 130 is placed and is free from deterioration due to an environment in a region in which the tube 130 is placed, for example, the bile duct, intestine duodenum, intestine jejunum, or intestine ileum. The material to be used for the tube 130 includes, for example, polyurethane, polyethylene, silicone, Teflon®, and rubber.

Figure 1:
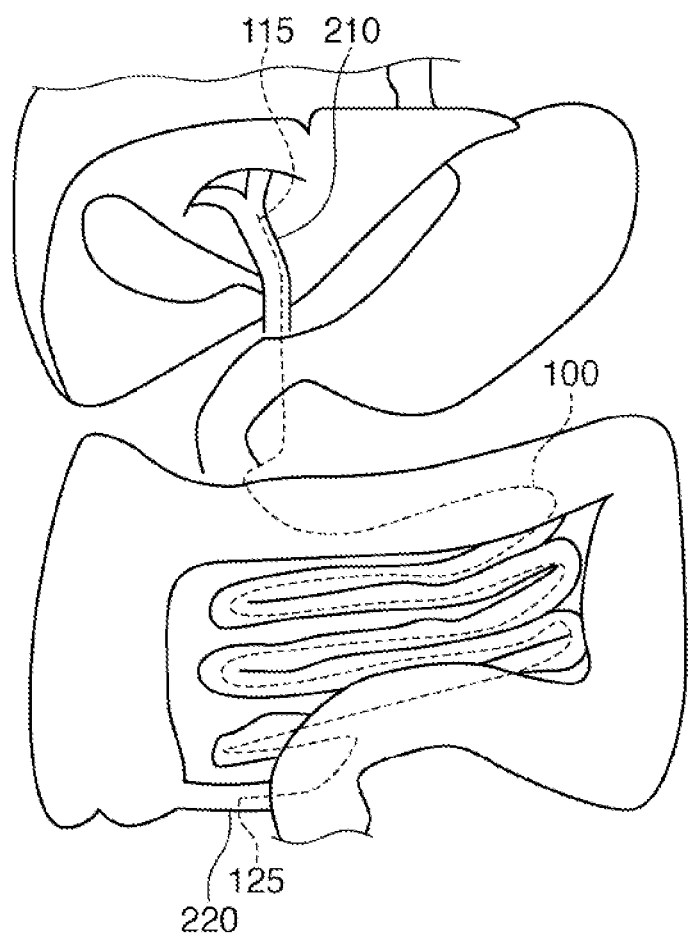
FIG. 1 is a view showing a method of using a tube 100 according to an embodiment of the presentinvention.
Figure 2:
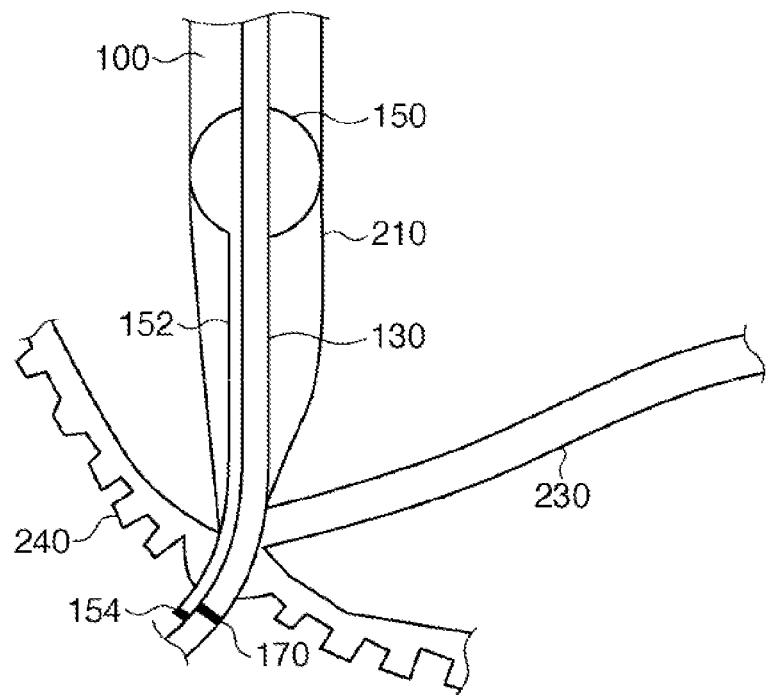
FIG. 2 is a view showing the location of the tube 100 in the bile duct according to the embodiment of the present invention.

An end portion 115 of the tube 130 according to this embodiment is inserted into a bile duct 210, as shown in FIGS. 1 and 2. Referring to FIG. 2, reference numeral 230 denotes a pancreatic duct; and 240, a Vater's papilla. The other end 125 of the tube 130 according to this embodiment is placed in an intestinal tract 220, as shown in FIG. 1. That is, as shown in FIG. 3, the tube 130 according to the embodiment has a portion A to be placed in the bile duct and a portion B to be placed in the intestinal tract. That is, the portion A to be placed in the bile duct is formed to have a diameter that allows insertion into the bile duct. In contrast, the portion B to be placed in the intestinal tract is formed to have a diameter that allows retention in the intestinal tract. A mark 170 may be added between the portion A and the portion B. The mark 170 is used to determine whether the portion A of the tube 130 is sufficiently inserted into the bile duct, when the tube 130 is inserted into the bile duct.

In this case, the portion A of the tube 130 which is placed in the bile duct and the portion B of the tube 130 which is placed in the intestinal tractmay have different arrangements. For example, the portion of the tube 130 which is inserted into the bile duct may differ in inner diameter, outer diameter, thickness, length, and material from the portion of the tube 130 which is placed in a region in the intestine duodenum, intestine jejunum, intestine ileum, and the like. More specifically, for example, the tube 130 can be configured such that the portion B to be placed in the intestinal tract is softer than the portion A to be placed in the bile duct. This can be implemented by using a softer material for the portion A than for the portion B or can be implemented by making the portion B of the tube 130 have a smaller thickness than the portion A of the tube 130. Making the portion A to be placed in the bile duct have higher hardness can prevent the occlusion of the tube 130 in the bile duct. In addition, making the portion B to be placed in the intestinal tract become softer can prevent damage to the intestinal tract.

The balloon 150 of the tube 100 according to this embodiment will be described next. The balloon 150 is a member having a void inside. That is, the balloon 150 can accommodate a gas or liquid. Injecting a gas or liquid into the balloon 150 can inflate it. In addition, removing the injected gas or liquid from the balloon 150 can deflate it. The balloon 150 will be described in detail below with reference to FIGS. 4A to 4C.

FIG. 4A shows a state in which the balloon 150 is inflated. FIG. 4C is a sectional view of the balloon 150 taken along a cutting plane S-S' in FIG. 4A. As shown in FIG. 4C, the tube 130 extends through the balloon 150. The balloon 150 can have a space independent of the inside of the tube 130. This space can exist outside the tube 130. In this case, it is possible to inflate the balloon 150 by injecting a gas or liquid into the inside of the balloon 150 and the outside of the tube 130.

Figure 4B:
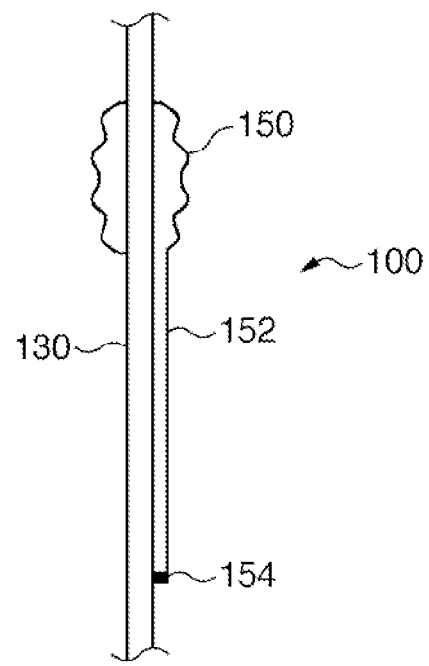
FIG. 4B is a sectional view of the tube 100 according to the embodiment of the present invention.
Figure 4C:
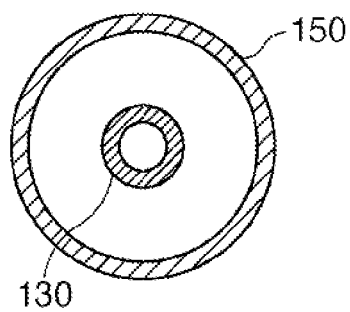
FIG. 4C is a sectional view of the tube 100 according to the embodiment of the present invention.

FIG. 4B shows a state in which the balloon 150 is deflated. The balloon 150 has an inlet 154. Injecting a gas or liquid into the balloon 150 through the inlet 154 can inflate the balloon 150, as shown in FIG. 4A. More specifically, the balloon 150 can inflate in the radial direction of the tube 100.

The inlet 154 can be anything having a structure that allows injection of an air or liquid into the balloon 150 and can hold the injected air or liquid inside, and can be, for example, a check valve or septum.

The inlet 154 may be placed on the surface of the balloon 150. However, since the balloon 150 is generally inserted into the bile duct, the inlet 154 placed outside the bile duct facilitates endoscopically inflating the balloon. The balloon 150 according to this embodiment can further include an injection tube 152. One end of the injection tube 152 is connected to the inside of the balloon 150. The other end of the injection tube 152 is provided with the inlet 154. The inlet 154 may be placed outside the bile duct, and may be inside the intestine duodenum. More specifically, the injection tube 152 may be formed to have a length that locates the inlet 154 outside the bile duct when the portion A of the tube 100 is inserted into the bile duct. Injecting a gas or liquid into the injection tube 152 through the inlet 154 can inflate the balloon 150. The injection tube 152 may be in tight contact with the tube 130. The injection tube 152 and the tube 130 can be integrally formed. For example, the tube 100 including the injection tube 152 and the tube 130 may have a nearly circular section perpendicular to its longitudinal direction. A cavity may be formed between the inner wall and outer wall of the tube 130 in the longitudinal direction and may be used as the injection tube 152. Forming the tube 100 in this manner can prevent the tube 130 from damaging the bile duct when the position of the tube 100 shifts.

When endoscopically injecting a gas or liquid by using a cannula, the needle may be inserted into the inlet 154 and the injection tube 152 to directly inject a gas or liquid into the balloon 150. In this case, the inlet 154 may be placed at any position on the injection tube 152, and may be placed at the contact point between the injection tube 152 and the balloon 150. In this case, the injection tube 152 may be formed to have a length that locates an end portion of the injection tube 152 which is not connected to the balloon 150 outside the bile duct when the portion A of the tube 100 is inserted into the bile duct.

The diameter (outer diameter) of the balloon 150 at the time of inflation may be 5 mm or more, and may be 7 mm or more. In addition, the diameter may be 11 mm or less, and may be 8 mm or less. Increasing the size of the balloon 150 can prevent the tube 100 from coming off the bile duct. Decreasing the size of the balloon 150 can reduce stimulus to the bile duct. In addition, the shape of the balloon 150 is not limited to a sphere. For example, the balloon 150 may have an elliptical shape, nearly triangular shape, or nearly rectangular shape. In order to avoid mechanical stimulus to the bile duct, the balloon 150 does not generally have a sharp shape, but may have an arbitrary shape.

The balloon 150 of the tube 100 according to this embodiment can exist at a position within 40 mm to 70 mm, or within 50 mm to 60 mm, from the end portion 115 of the tube 130 inserted into the bile duct. The tube 100 according to the embodiment may have only one balloon 150 or two or more balloons 150.

Having the balloon 150 in this manner allows the tube 100 according to this embodiment can prevent itself from unintentionally coming off the bile duct. In addition, sealing the bile duct with the balloon 150 allows a larger amount of bile to pass through the tube 130.

The material to be used for the balloon 150 is not specifically limited but can have a strength high enough not to be damaged when the tube 100 is placed and is free from deterioration due to an environment in a region in which the tube 100 is placed, for example, the bile duct. The material to be used for the balloon 150 includes, for example, polyurethane, polyethylene, silicone, Teflon®, and rubber.

If, the flow rate of bile is high and the viscosity of bile is low, it is possible to use the tube 100 having the structure shown in FIG. 4. If the tube clogs, the inner pressure of the bile duct increases. This causes cholangitis or bile duct stone formation. For this reason, when using the tube 100, using a cholagogue is effective in decreasing the viscosity of bile and increasing the flow rate. As another method, the tube 100 can further have a structure to prevent the tube from clogging.

Figure 5:
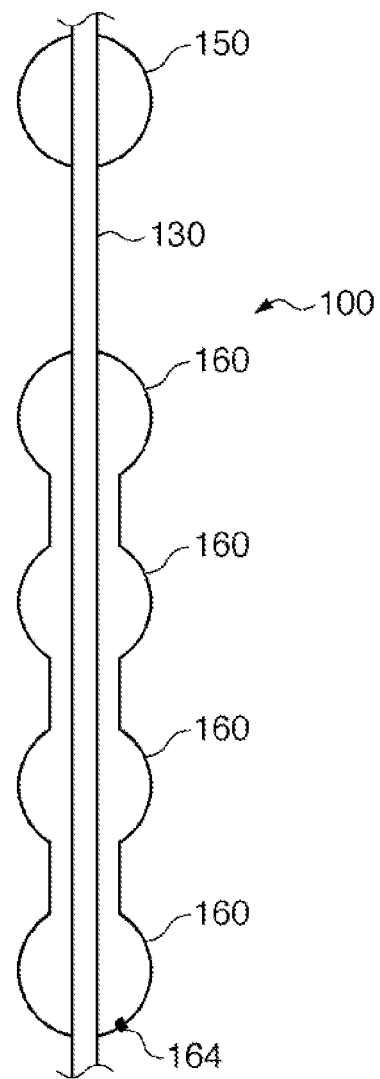
FIG. 5 is a sectional view of a tube 101 according to another embodiment of the present invention.

FIG. 5 shows the structure of a tube 101 according to another embodiment of the present invention. For the sake of easy understanding, FIG. 5 omits the illustration of an injection tube 152 and inlet 154. The tube 101 shown in FIG. 5 has one or more balloons 160, or two or more balloons 160, on a portion B placed in the intestinal tract. Each balloon 160 is a member capable of accommodating a gas or liquid inside. The balloon 160 can deflate and inflate as it accommodates a gas or liquid. Since the balloons 160 transmit the peristaltic waves of the intestinal tract to a tube 130, the tube 130 is milked in accordance with the peristalsis of the intestinal tract. This makes it possible for the tube 101 shown in FIG. 5 to more smoothly carry bile.

The diameter (outer diameter) of the balloon 160 at the time of inflation may be 5 mm or more, and may be 6 mm or more. In addition, the diameter may be 11 mm or less, and may be 8 mm or less. Furthermore, the shape of the balloon 160 is not limited to a sphere. For example, the balloon 160 may have an elliptical shape, nearly triangular shape, or nearly rectangular shape. In order to avoid mechanical stimulus to the intestinal tract, the balloon 160 does not generally have a sharp shape, but may have an arbitrary shape. The material to be used for the balloon 160 includes, for example, polyurethane, polyethylene, silicone, Teflon®, and rubber.

Each balloon 160 can have an inlet 164. The inlet 164 can be the same as the inlet 154. The lumens of the balloons 160 can be continuous. In this case, it is possible to inflate all the balloons 160 by injecting a gas or liquid from one inlet 164. That is, one balloon 160, or the balloon 160 nearest to the anus, may have the inlet 164.

Each balloon 160 described above is capable of deflating and inflating. However, the balloon 160 may keep inflating. For example, a gas, liquid, silicone, rubber, or the like may be initially injected into the balloon 160. Alternatively, the tube 130 may have a portion whose outer diameter is larger than that of the remaining portion instead of using the balloons 160. For example, a spherical member may be mounted on the tube 130. Such an arrangement can also perform milking of the tube 130.

A plurality of openings (side holes 110) can exist around an end portion 115 of the tube 130 which is placed in the bile duct. A plurality of openings (side holes 120) can exist around an end portion 125 of the tube 130 which is placed in the intestinal tract. Letting both the ends have holes in this manner allows bile to smoothly flow in and out of the tube 130.

For example, as shown in FIG. 3, the tube according to this embodiment can have the side holes 110 around the end portion 115 which is placed in the bile duct. In particular, the plurality of side holes 110 may be provided between the balloon 150 and the end portion 115 which is placed in the bile duct. In addition, as shown in FIG. 3, the tube according to this embodiment can have the side holes 120 throughout a predetermined length from the end portion 125 which is placed in the intestinal tract. The predetermined length can be, for example, 10 mm or more and 200 mm or less.

<Method of Using Tube According to Embodiment>

The tube 100 according to this embodiment can be used to adjust the dynamics of bile. More specifically, the tube 100 according to the embodiment has one end 115 placed in the bile duct and the other end 125 placed in the digestive organ nearer to the anus than the intersection point between the intestine duodenum and the bile duct. With this arrangement, bile is carried from one end 115 placed in the bile duct to the other end 125.

Placing the tube 100 according to this embodiment in the body in the above manner allows to expect to avoid the miscible state of food and bile. Avoiding the miscible state of food and bile can prevent the breakdown of fat. This suppresses the absorption of fat and hence allows to expect to improve obesity, especially severe obesity.

In addition, placing the tube 100 according to this embodiment in the body in the above manner allows to expect to prevent the regurgitation of bile into the stomach and the esophagus. As described above, the regurgitation of bile into the esophagus can be a cause of reflux esophagitis, Barrett's esophagus, and esophagus cancer. Using the tube 100 according to the embodiment allows to expect to improve or prevent such symptoms.

Figure 7:
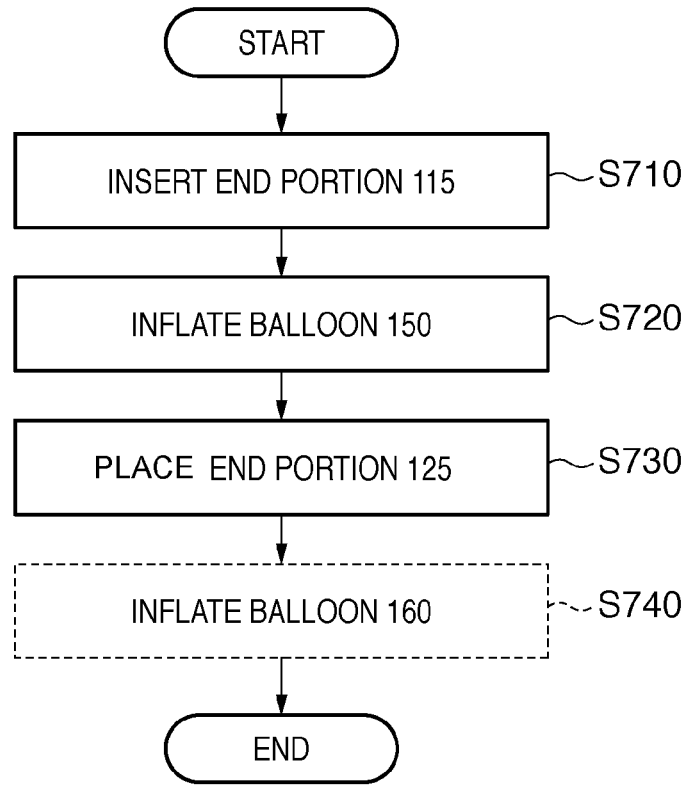
FIG. 7 is a flowchart for the method of placing the tube 100 according to the embodiment of the present invention.

A method of placing the tube 100 will be described in detail next with reference to the flowchart of FIG. 7.

Figure 6A:
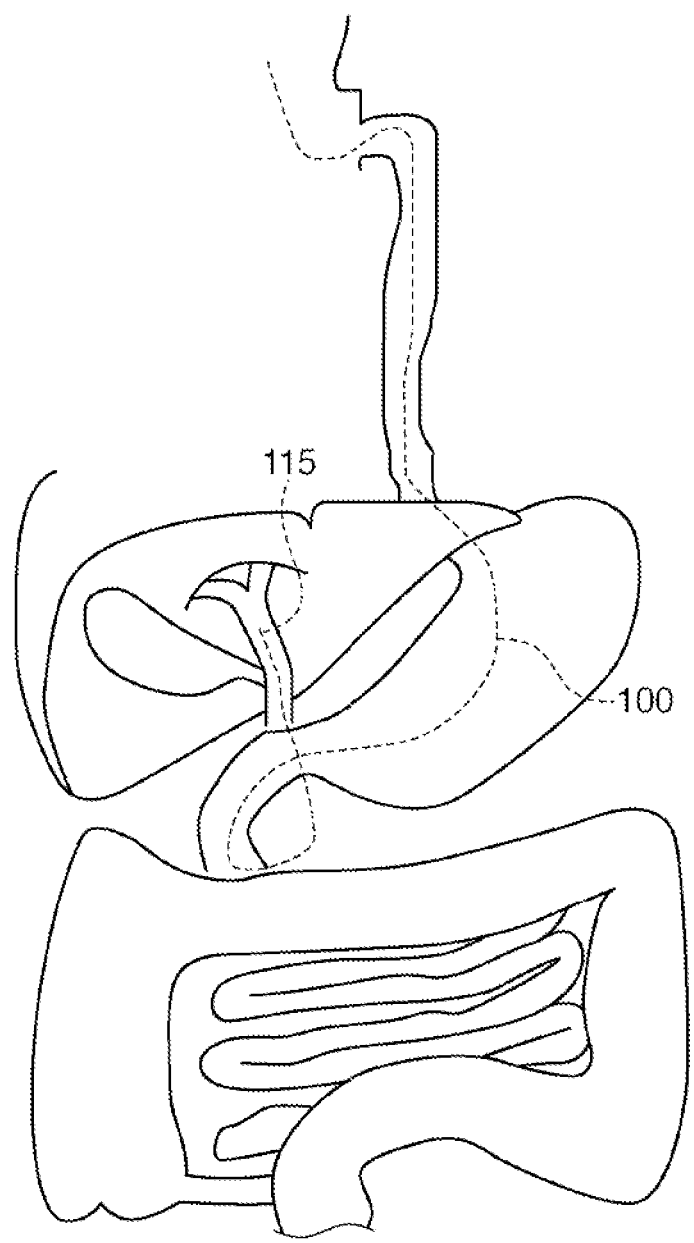
FIG. 6A is a view for explaining a method of placing the tube 100 according to the embodiment of the present invention.

In step S710, the operator inserts the end portion 115 of the tube 100 according to this embodiment into the bile duct. FIG. 6A shows a state in which the end portion 115 of the tube 100 is inserted into the bile duct. An arbitrary method can be used as a method of inserting the tube 100. In order to achieve low invasiveness, the operator can inserts the tube 100 by using an endoscope. More specifically, the operator can insert the tube 100 into the body and further insert the tube 100 into the intestine duodenum and the bile duct by using an orally or nasally inserted endoscope. For example, it is possible to perform this operation in the same manner as placing an internal fistularization biliary tractstent for bridging between the central portion and peripheral side of a constricted region at the time of medical treatment of obstructive jaundice. If the tube 100 has a mark 170, the operator may insert the tube 100 such that the mark 170 is located at the entrance of the biliary tract. If the tube 100 includes the injection tube 152, the end portion of the injection tube 152 which is located on the opposite side to the balloon 150 may be located outside the biliary tract.

In step S720, the balloon 150 is inflated. For example, injecting a gas like air or a liquid like water into the balloon 150 can inflate the balloon 150. Inflating the balloon 150 can prevent the tube 100 from unintentionally coming off the bile duct. As a concrete example of this, there is available a method of inflating the balloon 150 by inserting an injection pipe endoscopically inserted in the body into the balloon 150 through the inlet 154 and the injection tube 152 and injecting distilled water from the injection pipe. The operator may remove the injection pipe through the endoscope after injection.

It is also possible to deflate and inflate the balloon 150 without externally injecting any content. For example, the balloon 150 may accommodate a spring. In this case, it is possible to insert the tube 100 and the balloon 150 into the bile duct upon endoscopically pressurizing and deflating the balloon 150. In this case, the spring may be expandable to allow the tube 100 to be easily pulled out by deflating the balloon 150 when endoscopically pulling out the tube 100, although the tube 100 and the balloon 150 do not generally come out of the bile duct.

In step S730, the operator places the end portion 125 of the tube 100 according to this embodiment in a digestive organ. Although the end portion 125 may be placed in a digestive organ nearer to the anus than the intersection point between the intestine duodenum and the bile duct, the end portion 125 may be placed in the intestinum jejunum in consideration of the further suppression of the miscible state of food and bile and the prevention of the regurgitation of bile into the stomach and the esophagus. In consideration of the absorption of food in the intestinum jejunum and the intestinum ileum, the end portion 125 of the tube 100 can be placed at an end portion of the intestinum ileum, that is, a portion of the intestinum ileum which is located nearest to the anus or a portion nearer to the anus than the intestinum ileum.

Figure 6B:
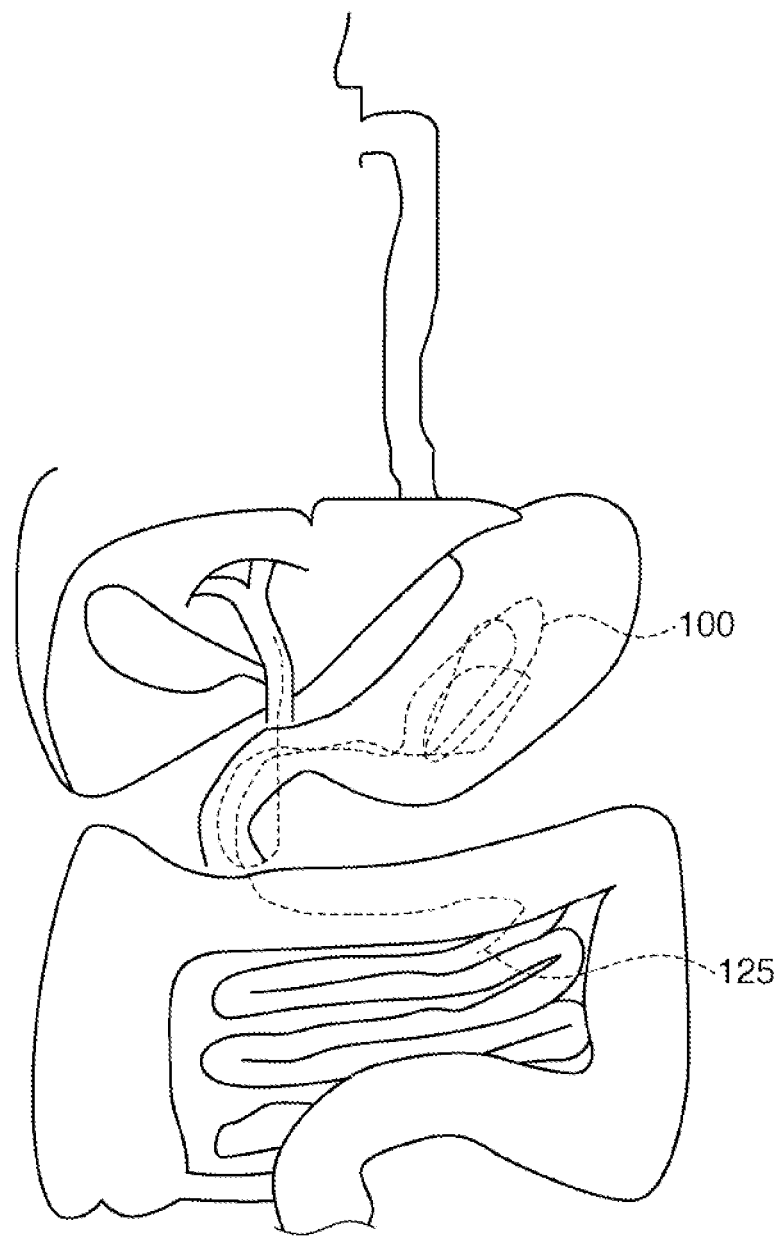
FIG. 6B is a view for explaining a method of placing the tube 100 according to the embodiment of the present invention.

As a concrete example of the method used in step S730, the following method is available. First of all, the operator temporarily places the tube 100 in the stomach by using an orally inserted endoscope. The operator then grips the end portion 125 to be placed in the intestine with the orally inserted endoscope and guides the end portion 125 to the position that the anally inserted endoscope can reach. The operator then may grip the end portion 125 by using the anally inserted endoscope and guide the end portion 125 to a proper region on an end portion of the intestinum ileum, as shown in FIG. 6B. As the anally inserted endoscope, for example, a small intestinal fiberscope can be used.

If the balloon 160 exists in a portion of the tube which is placed in the intestinal tract, the operator inflates the balloon 160 in step S740. It is possible to perform this operation by using the endoscope as in step S720. As a concrete example of this, the operator may inject distilled water from the inlet 164 of the balloon 160 by using the anally inserted endoscope.

Step S730 may not be executed. That is, the end portion 125 of the tube 100 is expected to foe carried to the intestinum ileum and the intestinum jejunum by the peristaltic motion of the digestive organ. It is also possible to execute step S740 without executing step S730. In this case, owing to the existence of the inflated balloon 160, the end portion 125 of the tube 100 is expected to be more smoothly carried to the intestinum ileum and the intestinum jejunum. In this case, the balloon 160 can be placed at the end portion 125 of the tube 100. The balloon 160 placed at the end portion 125 of the tube 100 can be formed from a material that dissolves in the intestinal tract in the end. In this case, it is possible to omit the step of deflating the balloon 160 when removing the tube 100.

In this embodiment, the step S730 may be executed before step S710. In addition, step S740 may be executed before step S710. Steps S730 and S740 may be executed in random order or concurrently.

Figure 8:
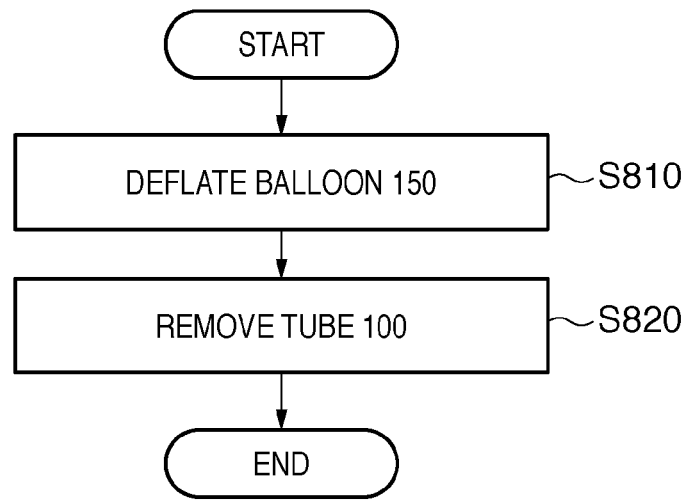
FIG. 8 is a flowchart for a method of removing the tube 100 according to the embodiment of the present invention.

A method of removing a tube will be described next with reference to the flowchart of FIG. 8. Although the operator can remove the tube according to this embodiment by an arbitrary method, he/she can uses an endoscope to achieve low invasiveness. When using the tube according to this embodiment to lose weight, the tube according to the embodiment can be endoscopically removed when a target weight is achieved. When using the tube according to the embodiment for medical treatment or prevention of reflux esophagitis, it is possible to easily remove the tube according to the embodiment upon achieving a reduction in the risk of shift from reflux esophagitis to Barrett esophagus, a reduction in the risk or the cure of reflux esophagitis, or the like.

In step S810, the operator deflates the balloon 150 in the bile duct. More specifically, the gas or liquid injected into the balloon 150 may be discharged. As a concrete example of this, the operator can discharge the gas or liquid injected into the balloon 150 by tearing off the injection tube 152 by using a biopsy forceps orally inserted through an endoscope. If the balloon 160 exists in the intestinal tract, the operator may also deflate the balloon. As a concrete example of this, the operator may perform the same operation as described above by using a biopsy forceps anally inserted through the endoscope.

In step S820, the operator pulls out the tube from the bile duct and further removes the tube 100 out of the body. For example, as conventionally practiced, it is possible to pull out the tube 100 by grasping it with a tripod forceps, basket forceps, or biopsy forceps. The tube 100 can be pulled out of the body through the inside of an endoscope which is orally, nasally, or anally inserted.

As described above, the tube according to this embodiment can be used for medical treatment for obesity or reflux esophagitis. Medical treatment using the tube according to this embodiment can be performed by using an endoscope, and hence it is possible to implement low-invasive treatment. Upon completion of medical treatment, it is possible to easily remove the tube according to this embodiment by using an endoscope. As has been described above, the tube according to the embodiment is an innovative technique positioned between pharmacological treatment and surgical treatment in the field of medical treatment for obesity or reflux esophagitis.

The present invention is not limited to the above embodiments and various changes and modifications can be made within the spirit and scope of the present invention. Therefore, to apprise the public of the scope of the present invention, the following claims are made.

What is claimed is:

1. A bile duct tube, comprising:
   a first portion which has a first end of the bile duct tube, the first portion adapted to be received in a bile duct;
   a second portion which has a second end of the bile duct tube, the second portion adapted to be received in intestinum jejunum or in intestinum ileum, or a digestive organ nearer to the anus than the intestinum ileum;
   a first expansion member placed at said first portion, wherein said first expansion member expands in a radial direction of the bile duct tube; and
   a plurality of second expansion members placed at said second portion, wherein said second expansion members are configured to be inflatable, said second expansion members being configured to transmit peristaltic waves of an intestinal tract to the bile duct tube and to make the bile duct tube carry bile.

2. The bile duct tube according to claim 1, further comprising an injection pipe for the gas or liquid, which is connected to said first expansion member,
   wherein said injection pipe includes a third end and a fourth end,
   said third end is connected to said first expansion member, and
   said injection pipe is formed to have a length that places said fourth end outside the bile duct when said first portion is inserted into the bile duct.

3. The bile duct tube according to claim 1, further comprising a plurality of openings at the second end of the bile duct tube, wherein inside of the bile duct tube and outside of the bile duct tube are connected through the plurality of openings.

4. The bile duct tube according to claim 1, wherein the bile duct tube is between about 1,400 mm to 1,800 mm.

5. A method of placing a bile duct tube in a body for adjusting the flow of bile in a body using the bile duct tube and for preventing or treating esophagus cancer, comprising:
inserting a first portion which has a first end of the bile duct tube into a bile duct from an intestine duodenum; and
placing a second portion which has a second end of the bile duct tube in intestinum jejunum or in intestinum ileum, or in a digestive organ nearer to the anus than the intestinum ileum,
whereby said bile duct tube carries bile through said bile duct tube from said first end to said second end to adjust the flow of bile, the method further including:
expanding a first expansion member placed at the first portion of the bile duct tube; and
expanding a plurality of second expansion members placed at the second portion of the bile duct tube.

6. The method according to claim 5, further comprising injecting a gas or liquid into a void inside the first expansion member placed at the first portion of the bile duct tube so that said first expansion member expands in a radial direction of the bile duct tube.

7. A method of adjusting the flow of bile in a body using a bile duct tube and preventing or treating reflux esophagitis, comprising:
providing a first portion which has a first end of the bile duct tube inserted in an bile duct; and
providing a second portion which has a second end of the bile duct tube placed in intestinum jejunum or intestinum ileum, or a digestive organ nearer to the anus than the intestinum ileum,
said bile duct tube carrying bile through said bile duct tube from said first end to said second end such as to adjust the flow of bile, the method further including:
expanding a first expansion member placed at the first portion of the bile duct tube; and
expanding a plurality of second expansion members placed at the second portion of the bile duct tube.

8. The method according to claim 7, further comprising injecting a gas or liquid into a void inside the first expansion member placed at the first portion of the bile duct tube so that said first expansion member expands in a radial direction of the bile duct tube, wherein the first portion has the first end portion.

9. The method according to claim 7, wherein the bile duct tube is maintained within the body until achieving a reduction of a risk of or the cure of reflux esophagitis.

10. The method of claim 7, wherein the bile duct tube suppresses the miscible state of food and bile in the body.

11. The method of claim 7, wherein the bile duct tube inhibits the regurgitation of bile into the stomach of the body.

12. The bile duct tube according to claim 1, wherein the second expansion members are made of material that dissolves in an intestinal tract.

13. The bile duct tube according to claim 1, wherein the first portion is made of a first material and the second portion is made of a second material, the first material is harder than the second material.

14. The bile duct tube according to claim 1, wherein the thickness of the bile duct tube is larger at the first portion than at the second portion.

15. The method according to claim 5, further comprising transmitting peristaltic waves of an intestinal tract to the bile duct tube through the plurality of second expansion members, wherein the peristaltic waves make the bile duct tube carry the bile.

16. The method according to claim 7, further comprising transmitting peristaltic waves of an intestinal tract to the bile duct tube through the plurality of second expansion members, wherein the peristaltic waves make the bile duct tube carry the bile.

17. The method according to claim 16, wherein the bile duct is placed in a body for the prevention or treatment of Barrett's esophagus.

18. The method according to claim 16, wherein the bile duct is placed in a body for the prevention or treatment of esophagus cancer.

* * * * *